United States Patent [19]

Charlton et al.

[11] Patent Number: 4,855,228

[45] Date of Patent: Aug. 8, 1989

[54] MULTIPLE OXIDATIVE INDICATOR SYSTEM FOR VISUAL DETERMINATION OF HYDROGEN PEROXIDE

[75] Inventors: Steven C. Charlton; Elva Kurchacova, both of Elkhart, Ind.

[73] Assignee: Miles Inc., Elkhart, Ind.

[21] Appl. No.: 95,143

[22] Filed: Sep. 11, 1987

[51] Int. Cl.$^4$ .................. C21Q 1/28; C21Q 1/54; C21Q 1/26; C12N 11/00

[52] U.S. Cl. ................................ 435/28; 435/14; 435/25; 435/174; 435/192; 435/805

[58] Field of Search .................. 435/14, 25, 26, 28, 435/805, 174, 192

[56] References Cited

U.S. PATENT DOCUMENTS

| | | | |
|---|---|---|---|
| 2,893,844 | 7/1959 | Cook | 435/14 |
| 2,981,606 | 4/1961 | Keston | 435/14 |
| 3,008,879 | 11/1961 | Harvill | 435/28 X |
| 4,042,329 | 8/1977 | Hochstrasser | 436/71 |
| 4,132,527 | 1/1979 | Maekawa et al. | 436/66 |
| 4,234,313 | 11/1980 | Faulkner | 436/99 |
| 4,716,110 | 12/1987 | Wada et al. | 435/28 X |

*Primary Examiner*—David M. Naff
*Attorney, Agent, or Firm*—Roger N. Coe

[57] ABSTRACT

The invention involves visual determination of hydrogen peroxide with a multiple oxidative indicator system capable of generating different hues at different concentrations of hydrogen peroxide or at different concentrations of an analyte from which hydrogen peroxide is generated by means of an analyte specific oxidase. A first indicator component of the multiple oxidative indicator system is oxidized from a particular hue to a different hue which is preferably essentially colorless. A second indicator component is oxidized to a hue which is visually distinct from the first indicator component in either of its hues. A third indicator component may also be present which is oxidized to provide a colorimetric response. Each component is oxidized only by hydrogen peroxide and peroxidase. The multiple oxidative indicator system is capable of generating visually distinct hues at different concentrations of hydrogen peroxide and can be used to generate a "rainbow" of hues when the indicator components are oxidized sequentially.

14 Claims, No Drawings

MULTIPLE OXIDATIVE INDICATOR SYSTEM FOR VISUAL DETERMINATION OF HYDROGEN PEROXIDE

FIELD OF THE INVENTION

The invention relates in general to test compositions for the visual determination of hydrogen peroxide and, in particular, to test compositions and test devices capable of generating different hues at different concentrations of hydrogen peroxide.

UTILITY

Colorimetric tests are conveniently used as visual tests with which relatively untrained personnel can routinely obtain results by simple comparison to an appropriate color chart. Visual tests are low cost and convenient since no instrumentation is required. Presently, visual tests are used for routine screening of urine samples for a number of diagnostically important analytes. For example, such tests are used by diabetics for home testing of urine or blood glucose and visual tests are also used in other fields including water testing for iron content. Many such tests are based on the detection of hydrogen peroxide in the presence of peroxidase and an oxidative indicator.

Currently available tests commonly relate the intensity of a particular color to the concentration of analyte. For example, a test device may change from colorless to light blue to darker shades of blue with increasing concentration of glucose. Greater visual discrimination, and therefore greater accuracy, is possible when a range of colors is provided rather than different shades or intensities of a single color. Therefore, a test composition which exhibits different colors (hues) at different analyte concentrations would be easier to use and would provide more accurate visual results.

The compositions of the invention provide a useful oxidative indicator system and are particularly useful for the visual determination of clinically important analytes, such as glucose and cholesterol, when an oxidase specific for the analyte of interest is added.

INFORMATION DISCLOSURE

Many systems have been devised for the colorimetric determination of hydrogen peroxide or analytes which can be determined by the use of hydrogen peroxide generating systems. Because of the importance of the determination of glucose, many of the detection systems disclose a glucose oxidase with a peroxidase/oxidative indicator system to provide a colorimetric output. The scope and extent of the literature and patents in the area of colorimetric testing based on the determination of hydrogen peroxide indicates that a great deal of time, effort and expertise has been utilized to provide better visual tests to the public.

U.S. Pat. No. 4,132,527, to Maekawa et al, is representative of patents which disclose the use of multiple oxidative indicators. However, each of the indicators is oxidized to a form having a distinct, visible color. The color apparent to the user is the summation of the colors of the oxidized indicators. Therefore, the apparent color of the reacted composition or strip becomes darker and darker with increasing concentration of analyte.

U.S. Pat. No. 4,234,313, to Faulkner, discloses a test composition for the determination of uric acid which uses an indicator composition which loses color with increasing amounts of uric acid present. The preferred indicator system is a complexed iodine source, starch-$I_2$, which is blue and loses color with increasing amounts of uric acid. Although Faulkner states that other compounds could be used, stating that, for example, "certain colored compounds undergo an irreversible change or loss of color on oxidation, with the formation of colorless products", no examples of indicators which become colorless on oxidation are disclosed.

In addition, some systems have been disclosed based on the generation of a colored indicator in which a second component reacts with the oxidized form (colored) of the indicator, reducing the oxidized indicator back to its colorless form. U.S. Pat. No. 4,042,329, to Hochstrasser, discloses such a system where the indicator is oxidized from a colorless form to a colored form but can be reduced back to the colorless form by a titrant. Only when the concentration of analyte is greater than the concentration of titrant, is color visible.

In U.S. Pat. No. 3,008,879, to Havill, a system is disclosed for the detection of glucose with an enzyme system composed of glucose oxidase and peroxidase, a primary indicator material which is oxidized to its colored form in the presence of hydrogen peroxide and peroxidase and a secondary indicator which is oxidized by the preferentially oxidized primary indicator and assumes its own particular colored form to produce a blended hue. The preferentially oxidized primary indicator material may be thus partially or completely returned to its reduced or colorless form.

German Pat. No. DE 32 47 894 discloses a reductive test system and method for the determination of reduced nicotine adenine dinucleotide, which produces an enlarged measuring range for the determination of NAD(P)H or substrates or enzymes reacting under the formation or consumption of NAD(P)H. The system is characterized in that it contains simultaneously several substances with different electrochemical potentials, functioning independently of one another as electron acceptors for NAD(P)H. The systems disclosed include the use of dichloroindophenol which is blue in the oxidized form, the unreacted form in a reductive system, and colorless in the reduced form, the reacted form in a reductive system. No mention is made or examples given of oxidative indicator systems.

None of the references discloses or suggests the use of multiple oxidative indicators, each reactive directly with hydrogen peroxide in the presence of peroxidase, at least one of which loses its hue on oxidation.

SUMMARY OF THE INVENTION

The invention is a test composition, test device and method for the visual determination of hydrogen peroxide in a fluid sample capable of generating different hues when contacted with different concentrations of hydrogen peroxide. Analytes which undergo reactions to produce hydrogen peroxide can also be detected with the addition of a hydrogen peroxide generating system. The test composition has a first apparent hue prior to contact with the fluid sample (i.e., unreacted) and a final apparent hue after contact with the fluid sample. The final apparent hue is visually distinct from the first apparent hue. The composition includes: a peroxidatively active substance and a multiple oxidative indicator system. The multiple oxidative indicator system is composed of at least a first and a second indicator component. The first indicator component has an apparent hue in its first form but loses this hue when oxidized to its second form. The second indicator component is capable of being oxidized to a form having a hue which is visually distinct from the first indicator component in either of its forms. The indicator component can be a single compound or a coupled indicator pair. The addition of a third oxidative indicator can be advantageous.

In preferred systems, the indicator components are oxidized sequentially so that a series of distinct hues (i.e., a "rainbow") is produced. Analytes of particular diagnostic interest, such as glucose, can be determined with the addition of an oxidase specific to that analyte, which oxidase is capable of generating hydrogen peroxide in the presence of the analyte. The composition can be incorporated into a carrier to provide a dry phase reagent strip. Compartmentalization of the indicators in different layers can improve the differentiation between hues seen at different concentrations of hydrogen peroxide. A convenient method of preparing the composition for a solution assay is also provided.

DESCRIPTION OF THE PREFERRED EMBODIMENTS

Visual color matching is convenient and can provide an acceptably accurate determination of analyte concentration without the need for expensive instrumentation. Usually, the "color" of the reacted test solution or test strip is matched, by eye, to blocks of color printed on a color chart. Matching is complicated by many factors: different visual perception of color from one person to another, lighting and the difference between the colors of a dry printed color on label stock and the colors seen in a reacted (i.e., wetted) paper or film test strip. However, a major complication is that the color blocks often exhibit differences of lightness or intensity of a single "color".

Although "color" is a commonly used term, color can be broken into components such as saturation, lightness and hue. Hue is commonly referred to as "color", e.g., whether something "looks" blue, red or yellow. Throughout the specification, the term "hue" shall be used to clarify the discussion. The invention contemplates changes in hue, not merely changes in lightness or saturation of a single hue.

Generally, one hue is associated with one form of a single indicator. Therefore, in order to generate a range of hues, a number of different indicator components or several forms of a single indicator component are required. However, the final hue of the typical test composition or device becomes progressively darker, moving toward black, as more hues are produced, unless there is some method for removing one hue. A great improvement in producing visually distinct hues has been found by using at least one indicator component which loses its hue on oxidation. Losing hue includes both the case where the oxidized form of the indicator is colored, but of a different hue to the unoxidized indicator, and the case where the oxidized form is colorless. The term "colorless" is defined herein to mean without visible hue and the expression "nearly colorless" is defined herein to mean having such a weak hue that the hue of the indicator does not effectively add to the apparent hue of the test composition.

The test compositions disclosed herein are useful for the determination of hydrogen peroxide. The compositions could be used with instruments having multiwavelength capability. However, they are particularly useful and expressly designed for visual testing. The test compositions are composed of a peroxidatively active substance and multiple oxidative indicator systems.

The multiple oxidative indicator system is composed of at least two oxidative indicator components. An oxidative indicator is defined as one which is capable of being oxidized in the presence of hydrogen peroxide and a peroxidatively active substance. The test composition is composed of a peroxidatively active substance and a first and second indicator component, each in the reduced form and each capable of being oxidized to produce a detectable response. The first indicator component (reduced) has one hue and is capable of being oxidized to a form which is of a different hue (including colorless). The second indicator component (reduced) is capable of being oxidized to a form having a hue which is visually distinct from the apparent hue of the the first indicator, oxidized or unoxidized. For example, if the first indicator component (reduced) is blue and the second indicator component (reduced) is colorless, the apparent hue of the unreacted test composition is blue. After contact of the test composition with the sample, both indicators are oxidized if hydrogen peroxide is present, and a hue other than blue will result depending on the concentration of hydrogen peroxide (or analyte), the sequence of the indicator reactions and the concentration of the indicator components relative to the concentration of hydrogen peroxide.

If the reactions are sequential and the concentration of hydrogen peroxide is sufficient to oxidize all indicator molecules, such that the first indicator component $C_1$ (reduced) is oxidized completely, or substantially completely, before the second indicator component $C_2$ (reduced) is oxidized; a dramatic color change can be produced. For example if $C_1$ (blue) is oxidized to $C'_1$ (colorless) and $C_2$ (colorless) is oxidized to $C'_2$ (red), the apparent hue of the test composition is blue and the apparent hue after reaction is red. This will produce a distinct change in hue from blue to red which can be much more easily followed by the user than various shades of blue. At lower concentrations of hydrogen peroxide, the apparent hue of the reacted test composition could be colorless. If the reactions of the indicators overlaps to some extent, i.e., not all of the first indicator component is oxidized before oxidation of the second indicator component begins, a mix of oxidized and reduced indicator components will result at some concentrations of hydrogen peroxide, producing a purple or another hue. More hues can be produced with the use of additional indicator components, each capable of being oxidized in the presence of hydrogen peroxide to produce a detectable change in the apparent hue of the reacted test composition.

Each indicator component can be a single compound or a pair of compounds forming a coupled indicator pair. The choice of the first oxidative indicator is particularly important. The number of indicators which lose hue on oxidation is much more limited than the number of indicators which become colorless on reduction because oxidation normally increases the conjugation of an indicator, which increase is commonly associated with the presence of color. However, the number of dye stuffs available is enormous and growing constantly. With the knowledge of the particularly advantageous results which can be obtained with such indicators, and with the guidance provided herein, many more such indicators can be found.

Acid Black #1, 4-amino-5-hydroxy-3-(p-nitrophenylazo)-6-(phenylazo)-2,7-naphthalenedisulfonic acid, disodium salt, (structure below) is a particularly preferred first oxidative indicator component.

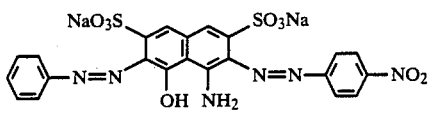

This compound is blue in the reduced form and colorless in the oxidized form. Besides Acid Black #1, several other indicators have been found which become so nearly colorless on oxidation that the contribution of the hue of the oxidized form, while visible as a very weak hue if oxidized alone, does not contribute to the hue of a reacted test composition. Among these are Nitro Red, Acid Orange 8, Acid Red #1, and Acid Red #4. The hues of the reduced and oxidized forms are shown in Table I. The structures of all these indicators are shown in the abbreviation portion of the Examples Section.

TABLE I

FIRST OXIDATIVE INDICATORS

| Common Name | Hue Reduced Form | Hue Oxidized Form |
| --- | --- | --- |
| Acid Black #1 | blue | colorless |
| Nitro Red | purple | weak blue/brown |
| Acid Orange #8 | strong orange | straw or very weak yellow |
| Acid Red #1 | orange | pale yellow |
| Acid Red #4 | pink/orange | light brown/light mauve |
| Acid Yellow #34 | yellow | colorless |
| Compounds 1 and 2 | red | cyan |

The structure of suitable compounds which become colorless on oxidation commonly contain a naphthalene ring with a diazo group ortho to a phenol or amine grouping as shown below:

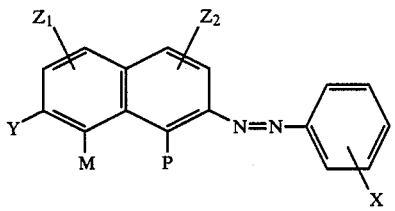

where:
M is H, OH, NH$_2$ or NH acetyl;
P is NH$_2$ or OH;
Z$_1$ and Z$_2$ are independently selected from H or —SO$_3$H or the salt thereof;
Y is H or a substituted phenyl azo ring; and
X is H or a substituent with OCH$_3$ and NO$_2$ being preferred. —NO$_2$ is particularly preferred.

For Acid Black #1, M is OH, P is NH$_2$, X is NO$_2$, Z$_1$ and Z$_2$ are NaSO$^-_3$ and Y is a phenylazo ring.

Other indicators which become nearly colorless on oxidation such as acid yellow #34 can also be used.

The hue of an indicator component can depend on the pH. Therefore in some cases it is desirable to control the pH of the test composition by adding a buffering substance.

The compounds available for the second, and optionally third or fourth, indicator component are very large. Indicators which exhibit a change in hue on oxidation include single and coupled indicators. These can include indicators which are oxidized from colorless to a form having a distinct hue, which constitute the vast majority of oxidative indicators, as well as indicators which are oxidized from one hue to another (color change indicators). Examples of the single indicator type include 3,3',5,5'-tetramethylbenzidine, o-toluidine and gum guaic; useful coupled indicators include 4-aminoantipyrine with 2-methyl indole, 4,5-dichloro-2-hydroxybenzenesulfonate (DCHBS) or CNSP.

A change of hue from a colorless reduced form to an oxidized form having an intense primary hue such as yellow, red or blue is preferred for a second indicator component. Most preferred is a test composition including a first indicator capable of being oxidized from blue to colorless, and second and third indicators capable of being oxidized from colorless to yellow and colorless to red. An oxidative rainbow is produced by a test composition which is blue when unreacted and which has apparent hues of green, yellow, orange and red at predetermined concentrations of hydrogen peroxide.

The peroxidatively active substance in the test composition is preferably peroxidase obtained from natural sources such as horseradish and potato. Other substances having peroxidative activity include inorganic compounds having peroxidase activity such as mixtures of potassium iodide and sodium molybdate, as well as other iodides, such as sodium and ammonium iodides, and other molybdates, such as potassium and ammonium molybdates, can be used. In addition, urohemin and a number of other porphyrin substances having peroxidative activity can be used. Various complex-forming compounds which activate metalloporphyrins, but which are not operable per se can be used therewith, such as 2-aminobenzothiazole, pyridine, bipyridyl, bipyridylpyridine, nicotinic acid or the like. Other substances which are not enzymes but have peroxidative activity include such compounds as iron sulfocyanate, iron tannate, ferrous ferrocyanide, potassium chromic sulfate and the like.

Additional components such as buffers, surfactants and stabilizers can also be added to the composition. The pH, and therefore the addition of a buffering substance, can determine the hue of a particular form of an indicator component. For example, Acid Orange 8 is oxidized from orange to a pale straw color at pH 7.5, but is oxidized to a (pale) yellow at pH 9.5. Nitro Red is oxidized from purple to a weak brown at pH 7.5, but is oxidized to a weak blue brown at pH 9.5. One pH condition can be more desirable than another to produce the desired range of hues. Many buffering substances are known to those skilled in the art and can be used, given that they do not interfere with the action of peroxidase and hydrogen peroxide to oxidize the indicator components.

The test composition can also be used to determine many analytes of diagnostic interest with the addition of an oxidase specific to that analyte and capable of producing hydrogen peroxide in the presence of that analyte. A list of particularly interesting analytes and their corresponding oxidases is shown in Table II below.

TABLE II

| | Analyte | Oxidase |
| --- | --- | --- |
| 1. | glucose | glucose oxidase |
| | Glucose + H$_2$O + O$_2$ $\xrightarrow{GO}$ Gluconic Acid + H$_2$O$_2$ | |
| 2. | alcohol | alcohol oxidase |

TABLE II-continued

| Analyte | Oxidase |
| --- | --- |

$$C_2H_5OH + O_2 \xrightarrow{AOD} CH_3CHO + H_2O_2$$

3.     cholesterol     cholesterol oxidase $$Cholesterol + O_2 \xrightarrow[\text{Oxidase}]{\text{Cholesterol}} Cholest\text{-}4\text{-}ene\text{-}3\text{-}one + H_2O_2$$

Other components may be required as additional components of the test composition. However, these reactions and their use in test compositions and dry phase test devices are well known in the art. The preferred pH for the test composition is often determined by the pH required for the oxidase enzyme. From that starting point, appropriate oxidative indicator components must then be chosen to produce the desired changes in hue.

The composition can be dissolved to provide a test solution or incorporated in a carrier matrix to provide a test device format. Either format can detect the presence of hydrogen peroxide in a body fluid or can detect the presence of some other analyte of interest when components are added to the test compositions to produce hydrogen peroxide from that analyte.

A convenient method of preparing a test solution can be found in the examples. Each component is dissolved in a separate solution of each indicator component or each part of a coupled pair is prepared. An enzyme solution containing peroxidase and the appropriate oxidase is prepared. Aliquots of each indicator and enzyme solutions are then combined to provide the test solution.

The balancing the concentrations of the indicator components will depend on the concentration range of the analyte to be determined and the predetermined concentration points which are most useful. For example, it would be preferred to produce one hue for a very low level of analyte (blue), green at the "normal" clinical range and red or orange at high or dangerous levels. This can be done with routine experimentation given the disclosure herein and the guidance provided in the examples. In addition to the ease with which an untrained layman can determine the results of a particular test, there is the advantage that a physician can rely upon the change in hues to simplify instructions to the layman.

The test composition can be provided as a test kit consisting of a solution or series of solutions to be mixed. However, dry phase reagent strips are well known and provide a useful format. The carrier matrix employed to produce a dry reagent strip can be any of several known in the industry, as long as the matrix can be incorporated with the composition and does not interfere with the reactions required for the production of color. These include paper; films such as those made from natural polymers, latexes, polyurethanes, silicones or combinations of these; and membranes such as microporous membranes such as those prepared by coagulation techniques from polyurethane.

Preformed carriers, such as paper, can be incorporated with the test composition by spraying, printing or dipping. The latter is preferred and is usually referred to as impregnation. Membranes can also be incorporated with the test composition(s) by these techniques. These membranes have the added advantage that one or more of the components can be added when the membrane is prepared, providing a uniform distribution within the membrane. It is commonly preferred to add one or more of the indicators during the formation of the membrane, then to add other components, such as enzyme and buffers, by incorporation, most preferably by impregnation.

A paper or membrane carrier can be mounted on a rigid backing or support member with double sided adhesive. The membranes or films can also be formed directly on a support. Such supports are commonly water impervious rigid polymer films such as polyethylene terephthalate, polystyrene, polyester or the like. The support forms a convenient handle for the user since the reagent area required for such tests is very small. The backing can be opaque or transparent, although an opaque white backing is preferred for visually read tests. Additional layers can be added to the test device to permit wiping or removal of red blood cells from the surface prior to reading. This can be accomplished by polymer coating or by the addition of a layer which filters the red blood cells which can be wiped or the layer itself removed.

Indicator components can be isolated in separate layers of a multilayer test device. Such layers can be produced by known techniques either on paper membranes or with films. This can provide additional color differentiation and can provide a convenient manner to control the order of development of hues in final device. Multilayered gelatin film matrices have been found to be especially useful for this purpose.

This description provides sufficient information to produce test compositions or test devices for the determination of hydrogen peroxide or diagnostic analytes which will generate visually distinct hues at different concentrations of hydrogen peroxide. The hydrogen peroxide can be generated by an oxidase system from many analytes of clinical interest. The invention requires the use of at least two indicator components. The first indicator component must lose its hue on oxidation either to a colorless form or at least to a different hue. The second indicator component must also change hues, e.g., go from a colorless reduced form to an oxidized form having a distinct, relatively intense hue. The hues which can be generated are as varied as the number of oxidative indicator compounds available. The final apparent hue of the composition will also depend on the relative concentrations of the indicator components. This fact can be used to shift the range of hues available and the analyte concentrations where a shift in hue is apparent.

The invention will now be illustrated by Examples. However, no limitation of the invention should be implied from the examples as the scope of the invention is defined by the claims. Those skilled in the art will be able to make many variations given the disclosure.

EXAMPLES

| Abbreviations | |
| --- | --- |
| HEPES | buffer, N—2-hydroxyethyl piperazine-N'—2-ethane sulfonic acid |
| TAPSO | buffer, 3-(N—tris(hydroxymethyl)methylamino)-2-hydroxypropanesulfonic acid |
| TRIS | buffer, Tris(hydroxymethyl)aminomethane |
| (tris$_2$SO$_4$ | Tris buffer adjusted to the given pH value with sulphuric acid. |
| Triton ® X-100 | surfactant, polyoxyethylene ether available from Sigma |

| | |
|---|---|
| | Chemical Co. |
| U | International Units, a measure of enzyme activity (one U is the enzyme activity required to catalyze the conversation of one micromole of substrate per minute under specified conditions of temperature and pH) |
| Me | methyl |
| POD | peroxidase |
| GO | glucose oxidase |
| AOD | alcohol oxidase |
| PET | polyethylene terephthalate |
| dL | deciliters |
| mL | milliliters |
| μL | microliters |
| g | grams |
| μ | microns |
| RT | room temperature, usually 25° C. |
| MW | molecular weight |
| qs | added to produce the volume |
| In The Tables | |
| φ | hue visually distinct |
| = | hue visually indistinguishable |
| Color Abbreviations | |
| OR | orange |
| R | red |
| Pk | pink |
| Bl | blue |
| Br | brown |
| Gn | green |
| Gr | grey |
| Mau | mauve |
| Y | yellow |
| L. | light |
| Compound Abbreviations | |
| 4AP | 4-aminoantipyrine |
| DCHBS | 3,5-dichloro-2-hydroxy-benzene sulfonate |

INDICATORS

Nitro red (Compound 4)

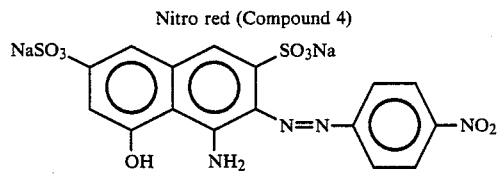

Acid orange 8 (Compound 6)

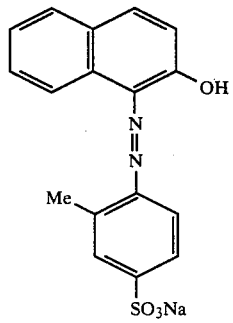

Acid Red 1

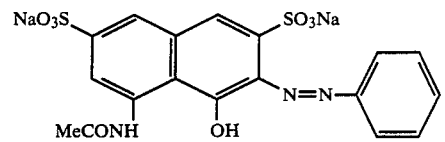

Acid Red 4

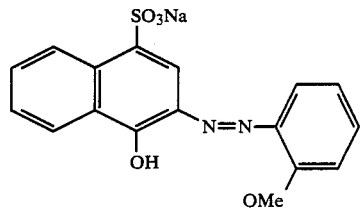

Acid Yellow 34

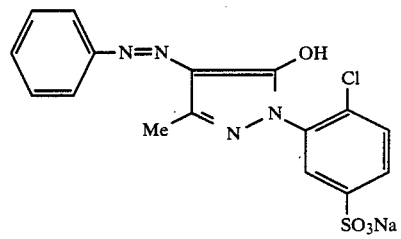

CNSP (RNG-3608) - 3-carboxy-4-[4''-(2''-N-4-(2''',4'''-bis-tert-amyl-phenoxy)butylcarbamoyl)-1''-hydroxynaphthloxy-phenylazo]-1-sulfophenyl-5-pyrazolone

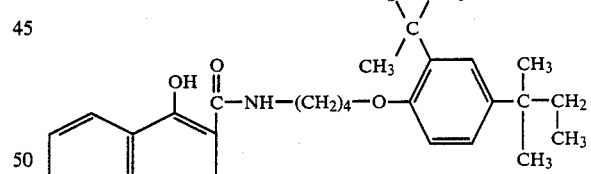
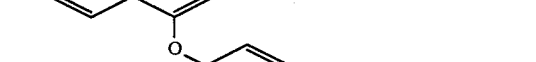
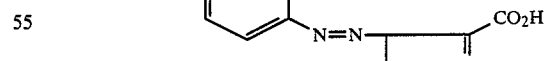

1-(4-phenoxy-3-sulfophenyl)-3(octadecamido)-5-pyrazolone (Compound 7)

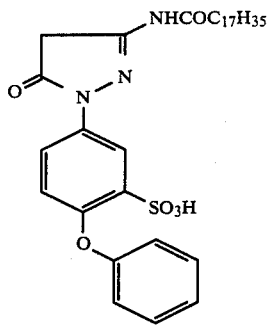

N,N-diethyl-p-phenylenediamine (Compound 1)

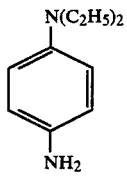

1-hydroxy-4-(2'-N'-tolyl-N-sulfamoylamine)phenylazo-2-N-(2''-N''-methyl-N''-octadecyl)phenylnaphthoamide (Compound 2)

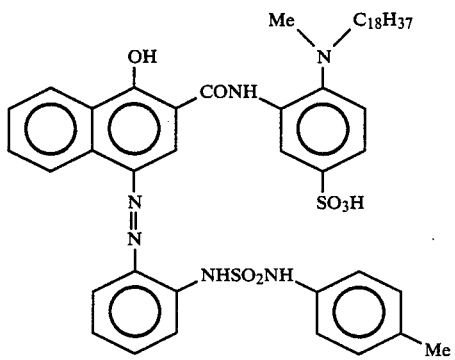

N-[2'-octadecyloxy-5-(N-methylsulfamoyl)]phenyl-2-(4-methoxy)benzoylacetanilide (Compound 3)

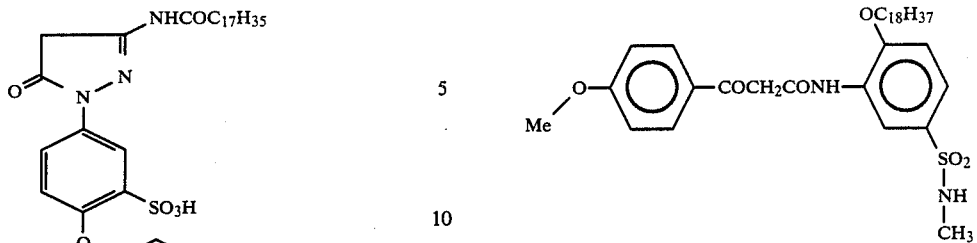

EXAMPLE 1

GENERATION OF DIFFERENT HUES BY REACTION WITH HYDROGEN PEROXIDE

Two test compositions were prepared with different multiple oxidative indicator systems, which were capable of generating different hues in response to increasing concentrations of hydrogen peroxide. The test compositions were tested as solutions with the addition of hydrogen peroxide. In order to facilitate color comparison, an aliquot (30 μL) of the reacted solution was applied to plain white paper. The end point was reached in about two to four minutes.

A. A multi-oxidative indicator system was prepared using Nitro Red as the first indicator component which changes from a colored form to a colorless form and 2-amino-3-hydroxy-5-bromopyridine as the second indicator component. Nitro Red is oxidized in the presence of hydrogen peroxide and peroxidase from purple to a very weak blue/brown. While the oxidized form can be seen if the first indicator component is oxidized by itself, the color produced is so weak that it contributes little, if any, visible color in a multi-indicator system. The second indicator component is oxidized from colorless to a strong yellow.

Solutions of these two compounds were made for the assay of hydrogen peroxide. (Table 1) The test solutions also contained a buffer, $(tris)_2SO_4$, 0.1M pH 8.5, and peroxidase (20 U/mL). Hydrogen peroxide was added to aliquots of test solutions and after endpoint was reached in approximately 2 to 4 minutes, 30 μL of each reacted solution was applied to a plain piece of absorbent filter paper so that the hues produced could be compared.

With these solutions a range of hues can be seen which corresponds to the increasing concentrations of hydrogen peroxide, i.e., blue at low concentration, green at an intermediate concentration, yellow at high concentration.

TABLE 1

| Nitro Red (mM) | 2-amino-3-hydroxy-5-bromopyridine (mM) | [H$_2$O$_2$] (mM) | | | | | | |
|---|---|---|---|---|---|---|---|---|
| | | 0 | .1 | ,.2 | .5 | .75 | 1 | 1.5 |
| .0625 | 1.5 | Bl-Mau | φFaint Mau | φBl-Gr | φGn-Bl | φlGn | φLess Gn | φY |
| .0375 | 1.5 | Bl-Mau | φBl-Gn | φGn-Bl | φLime Gn | =Lime Gn | φY | φDeeper Yellow |
| .0375 | 0 | Bl-Mau | φFaint Pk | = | = | = | = | = |

B. A second multi-oxidative indicator system was prepared using Acid Orange 8 (compound 6) as the first indicator component and compounds 1 and 7 a coupled indicator pair which form the second indicator component. Acid Orange 8 (compound 6) is oxidized in the presence of hydrogen peroxide and peroxidase from strong orange to a very weak yellow or straw color. While the hue of the oxidized form can be distinguished visually if oxidized alone and placed near a white background, the hue is so pale that there is little, if any, visual contribution when in combination with other colored indicators. Compound 7 is oxidized in the presence of compound 1, hydrogen peroxide and peroxidase from a colorless form to magenta. The test solutions were prepared and tested as shown in part A. Results are shown in Table 2 below. Similar differentiation was obtained although the final hues were different.

gradation of the same hue. High concentrations can be more easily determined since the apparent hues have not become so dark as to be visually indistinguishable.

EXAMPLE 3

RAINBOW GENERATION FOR THE DETERMINATION OF GLUCOSE

Acid Black #1 is a preferred first indicator component because it is blue in the reduced form and colorless when oxidized in the presence of hydrogen peroxide and peroxidase. This compound provided the starting point for a multi-indicator system capable of producing the hues of the rainbow with increasing concentrations of glucose. This result is particularly preferred since the generation of distinct hues, blue to green to red, pro-

TABLE 2

| Acid Orange 8 (mM) | [Compound 1] (mM) | [Compound 7] (mM) | [H$_2$O$_2$] (mM) | | | | | | |
|---|---|---|---|---|---|---|---|---|---|
| | | | 0 | .1 | .2 | .5 | .75 | 1.0 | 1.5 |
| 0.8 | 0.25 | 0.5 | Y-Or | φTan | φOR-Mau | φMau | =Mau | φPurple | =Purple |
| 0.4 | 0.25 | 0.5 | L.Y-Or | φOr-R | φL.Mau | φStrong Mau | φStrong Mau | = | = |

EXAMPLE 2

MULTIHUE GENERATION FOR THE DETERMINATION OF GLUCOSE

A test device for the determination of glucose capable of generating different hues at different concentrations of glucose using glucose oxidase as the hydrogen peroxide generating system was prepared.

The test solution included glucose oxidase (50 U/mL), peroxidase (50 U/mL), TAPSO (pH 8.5, 20 mM) and polyvinyl alcohol (88% hydrolyzed, 10,000 MW, 1.5% weight to weight) and compounds 1, 2 and 3 as indicator components. Compound 2 (red-pink) when oxidatively coupled with compound 1 through the action of hydrogen peroxide and peroxidase generates a cyan hue. In the same way, compound 3 (colorless) produces yellow when oxidatively coupled with compound 1. The ratios of indicator components used are shown in Table 3.

Whatman 31 ET filter paper was dipped into the above solution and dried. The paper was cut into strips and tested with glucose solutions, buffered with (tris)-$_2$SO$_4$, 0.1M, pH 8.5.

End-point hues were achieved in about 10 minutes and are also shown in the Table.

vides the greatest visual discrimination for diabetics.

The test composition was formulated with a first indicator component, Acid Black #1, a second indicator component, 3,5-dichloro-2-hydroxybenzene sulfonate (DCHBS) and 4-aminoantipyrine (4-AP); and a third indicator component, 2-methylindole and 4-aminoantipyrine. The changes in hue available from these indicators on oxidation are shown below.

| | Reduced | Oxidized |
|---|---|---|
| 1. Acid Black #1 | blue | colorless |
| 2. 4-AP and DCHBS | colorless | orange |
| 3. 4-AP and 2 methylindole | brown | orange |

A test composition was prepared as follows:

| Formulation #1 | |
|---|---|
| Acid Black #1 | 60 mg |
| 4-AP | 365 mg |
| DCHBS | 50 mg |
| H$_2$O qs | 100 mL |
| Formulation #2 | |
| Glucose oxidase (1,221 U/mL) | 20 mL |
| Peroxidase (60 U/mg) | 1 g |

TABLE 3

| [Compound 1] (mM) | [Compound 2] (mM) | [Compound 3] (mM) | Glucose (mM) | | | | | | |
|---|---|---|---|---|---|---|---|---|---|
| | | | 0 | .5 | 1.0 | 2.0 | 3.75 | 7.5 | 15 |
| 1.5 | 0.75 | 0.75 | Pk | φPk-Or | φOr-Pk | φOr-Gn | φGn | φLime Gn | =Lime Gn |
| 1.5 | 0.5 | 1.0 | Pk | φPk-Or | φOr | φGn-Y | φY | φPale Lime Gn | = |
| 1.5 | 1.0 | 0.5 | Pk | φPk-Or | φOr-Br | φPale Gn | φLime Gn | | |
| 1.5 | 0.75 | 0 | Pk-Mau | φMau-Gn | φGn-Mau | Cyan | | | |

The hues produced can be changed by varying the ratio of compounds 2 and 3, e.g., at a level of 1 μM, the hue generated can be OR-PK, OR, OR-Br or Gn-Mau. By adding an additional indicator, the hues orange, tan and brown are added. The last experiment shown on Table 3 is a control.

The experiment showed that different hues can be generated which can be related to the increasing concentration of glucose in a test sample. These hues can be more easily distinguished than variations in intensity or

| Formulation #3 | |
|---|---|
| Formulation #1 | 2 mL |
| Formulation #2 | 2 mL |
| 4-AP (10$^{-2}$ M) | 1 mL |
| 2-Methylindole (10$^{-2}$M) | 1 mL |

Procedure: 100 μL of Formulation #3 was mixed with 100 μL of an aqueous solution containing different concentrations of glucose. After two minutes, the hue of the test solutions was determined by placing an aliquot of each solution on a piece of filter paper.

| Glucose Concentration | Hue |
| --- | --- |
| 0 | Blue |
| 50 mg/dL | Green-blue |
| 200 mg/dL | Moss green |
| 1000 mg/dL | Orange-red |

At increasing concentrations of glucose, distinct hues (blue, green, orange) were produced.

B. A second set of solutions was prepared based on the formulations #1 and #2 above, and a different third indicator component, CNSP. This indicator changes from yellow in the reduced form to red in the oxidized form. Therefore, the hue of the composition when no glucose was present was green and the hues generated upon oxidation were different from those seen in Example 3A. However, visually distinct hues were provided by this composition also.

| Formulation #4: | |
| --- | --- |
| Formulation #1 | 2 mL |
| Formulation #2 | 2 mL |
| 4-AP ($10^{-2}$M) | 2 mL |
| CNSP ($10^{-2}$M) | 2 mL |

Procedure: 100 μL Formula #4 was mixed with 100 μL of an aqueous solution containing different concentrations of glucose. After one to two minutes, the hues of the solutions were determined as in part A.

| Glucose Concentration | Hue |
| --- | --- |
| 0 | Green |
| 50 mg/dL | Moss Green |
| 200 mg/dL | Brown |
| 1000 mg/dL | Orange-red |

Once again easily distinguishable hues were produced over a wide concentration range of glucose.

Obviously, many modifications and variations of the invention as hereinbefore set forth can be made without departing from the spirit and scope thereof and therefore only such limitations should be imposed as are indicated by the appended claims.

What is claimed is:

1. A test composition for the visual determination of hydrogen peroxide in a fluid sample, comprising a composition having a first apparent color prior to contact with a fluid sample and a final apparent color after contact with the fluid sample, wherein the final apparent color is visually distinct from the first apparent color and depends on the concentration of hydrogen peroxide in the fluid sample, said test composition comprising:
  (a) a peroxidatively active substance; and
  (b) a multiple oxidative indicator system, which multiple oxidative indicator system is composed of at least a first and a second oxidative indicator component, each indicator component of the system being oxidized only by hydrogen peroxide and the peroxidatively active substance; and wherein the first indicator component is oxidized from a first apparent color to essentially colorless and the second indicator component is oxidized to a final apparent color which is visually distinct from the first apparent color.

2. The test composition of claim 1, wherein the multiple oxidative indicator system is additionally composed of a third oxidative indicator capable of being oxidized in the presence of hydrogen peroxide and the peroxidatively active substance to provide a colorimetric response.

3. The test composition of claim 1, which additionally comprises a buffering substance.

4. The test composition of claim 1, in which the peroxidatively active substance is peroxidase.

5. The test composition of claim 1, which additionally comprises an enzyme system capable of generating hydrogen peroxide from an analyte in the fluid sample.

6. The test composition of claim 5, in which the enzyme system includes an oxidase.

7. The test composition of claim 1, in which the first indicator component is Acid Black #1.

8. The test composition of claim 1, in which the first indicator component has the structure

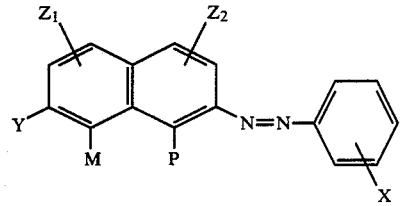

wherein
M is H, OH, $NH_2$ or NH Acetyl;
P is $NH_2$ or OH;
$Z$ and $Z_2$ are independently selected from H or $-SO_3H$ or the salt thereof;
Y is H or a substituted phenyl azo ring; and
X is $-NO_2$.

9. A test composition for the visual determination of hydrogen peroxide in a fluid sample, comprising:
  a composition having a first apparent color prior to contact with a fluid sample and a final apparent color after contact with the fluid sample, wherein the final apparent color is visually distinct from the first apparent color and depends on the concentration of hydrogen peroxide in the fluid sample, said test composition comprising:
  (a) peroxidase; and
  (b) a multiple oxidative indicator system composed of Acid Black #1 and at least a second oxidative indicator component capable of being oxidized only by hydrogen peroxide and peroxidase to produce a colorimetric response; and wherein the Acid Black #1 is oxidized from a first apparent color to essentially colorless and the second oxidative indicator component is oxidized to a final apparent color which is visually distinct from the first apparent color.

10. The test composition of claim 9, which additionally comprises an enzyme system capable of generating hydrogen peroxide from an analyte present in the fluid sample.

11. A test composition for the visual determination of an analyte in a fluid sample, comprising:
  a. an enzyme system capable of generating hydrogen peroxide from an analyte of interest;

b. peroxidase; and
c. a multiple indicator system composed of Acid Black #1, and two coupled oxidative indicator components, 4-aminoantipyrine/2-methylindole and 4-aminoantipyrine/3,5-dichloro-2-hydroxybenzene sulfonate.

12. A test device for the determination of hydrogen peroxide, said test device comprising:
   (a) a carrier matrix, and
   (b) a test composition incorporated into the carrier matrix, said test composition comprising a peroxidase and a multiple oxidative indicator system, which indicator system is composed of at least a first and a second oxidative indicator component, each indicator component of the system being oxidized only by hydrogen peroxide and peroxidase; and wherein the first oxidative indicator component is oxidized from a first apparent color to essentially colorless and the second indicator component is oxidized to a final apparent color which is visually distinct from the first apparent color.

13. The test device of claim 12, in which at least one indicator component is present in the carrier matrix as a layer.

14. The test device of claim 12, in which the first oxidative indicator component is Acid Black #1.

* * * * *